United States Patent [19]
Cohen et al.

[11] Patent Number: 5,295,977
[45] Date of Patent: Mar. 22, 1994

[54] TROCAR CATHETER FOR DRAINAGE

[75] Inventors: Herbert Cohen, Fort Lauderdale; Frank A. Scarfone, Boca Raton; David Turkel, Miami, all of Fla.

[73] Assignee: Symbiosis Corporation, Miami, Fla.

[21] Appl. No.: 64,461

[22] Filed: May 11, 1993

[51] Int. Cl.⁵ .................. A61M 5/00; A61M 5/178
[52] U.S. Cl. ........................ 604/264; 604/164
[58] Field of Search .............. 604/51, 136, 157, 164, 604/170, 264, 272–274, 117; 606/185, 188

[56] References Cited

U.S. PATENT DOCUMENTS 5,066,288 11/1991 Deniega et al. ................ 604/164

Primary Examiner—C. Fred Rosenbaum
Assistant Examiner—Frank Wilkens, III
Attorney, Agent, or Firm—David P. Gordon

[57] ABSTRACT

A trocar catheter includes a trocar rod having a stepped diameter distal end for use with a catheter having a stepped diameter lumen wherein the trocar is inserted into the lumen of the catheter and the trocar is used to incise a patient and install the catheter after which the trocar is removed from the lumen of the catheter. The distal end of the trocar rod is provided with a stepped coaxial bore into which a piercing point rod, a spring and a safety sleeve are assembled. The piercing point rod has a proximal small diameter portion which is press fit into a correspondingly small diameter portion of the coaxial bore in the distal end of the trocar rod. The spring is carried on the small diameter portion of the piercing point rod and biases the safety sleeve in a distal direction. The distal end of the piercing point rod has a larger diameter portion tapering to a piercing tip and the safety sleeve has a stepped inner diameter which prevents it from moving beyond a predetermined distal position covering the piercing tip. The stepped coaxial bore has a large diameter portion for receiving the safety sleeve when it is pressed proximally against the spring. A protrusion on the distal outer surface of the safety sleeve prevents the catheter from accidentally slipping off the trocar.

19 Claims, 3 Drawing Sheets

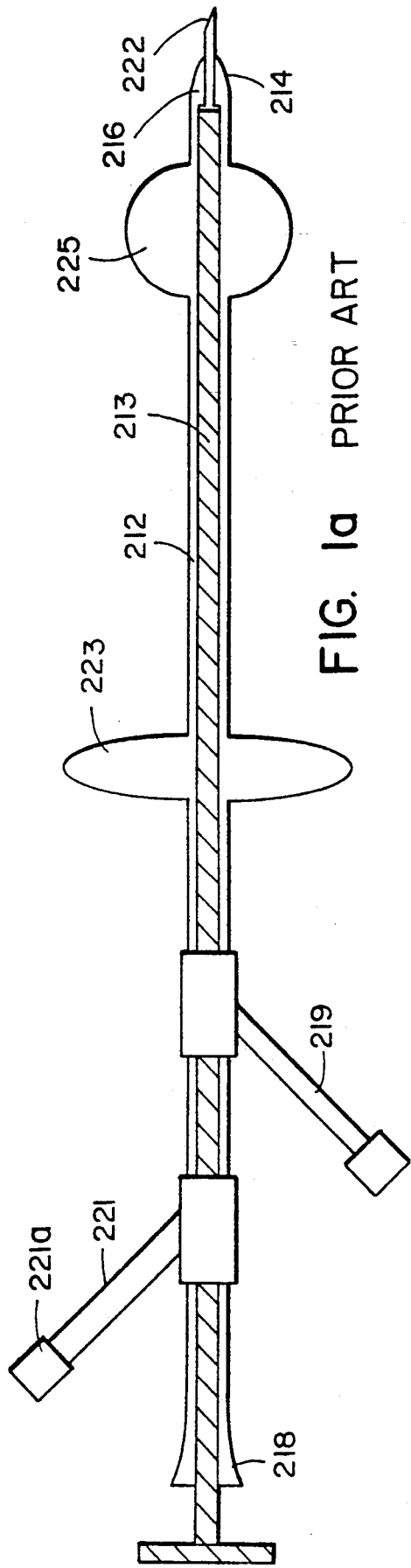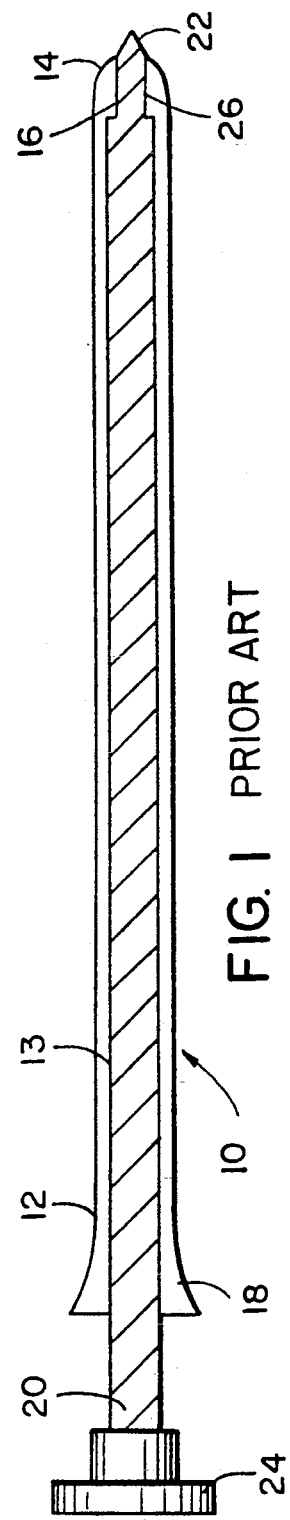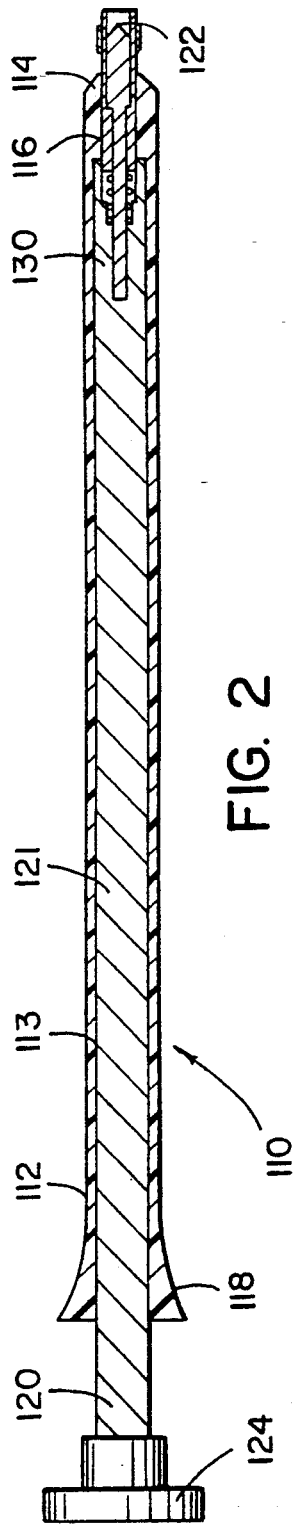
FIG. 1a PRIOR ART
FIG. 1 PRIOR ART
FIG. 2

TROCAR CATHETER FOR DRAINAGE

BACKGROUND OF THE INVENTION

1. Field of the Invention

This invention relates to a surgical trocar catheter for drainage. More particularly, this invention relates to a trocar for use with a drainage catheter where the trocar has a spring biased safety shield mechanism.

2. State of the Art

Trocar catheters for drainage are well known in the surgical arts. These devices generally include a flexible, partially elastic catheter and a metal trocar which is removably inserted into the catheter. One such known device is a chest drainage trocar catheter shown schematically in longitudinal cross section in prior art FIG. 1 The prior art chest drainage trocar catheter device 10 includes a flexible partially elastic catheter 12 which is approximately nine and one half inches long having a cross section of approximately one quarter of an inch and an inner diameter defining a lumen 13 of approximately one eighth of an inch. The lumen 13 has a stepped smaller diameter portion 16 at the distal end 14 of the catheter. The proximal end 18 of the catheter is flared for coupling with a drainage conduit or syringe (not shown). The distal end of the catheter preferably includes a plurality of openings or ports (not shown) for drainage. A metal trocar 20 approximately eleven inches long having an outer diameter of approximately one eighth of an inch is inserted into the lumen 13 of the catheter 12. The distal end of the trocar has a piercing point 22 and the proximal end of the trocar has a small circular gripping or pushing plastic base 24. The piercing point 22 of the trocar has a stepped smaller outer diameter 26 which mates with the stepped smaller inner diameter 16 of the distal end of the catheter so that the piercing point extends a predetermined fixed length beyond the distal end of the catheter. The trocar 20 is thereby prevented from passing beyond that point through the catheter. The stepped diameters of the trocar and catheter also insure that forward movement of the trocar 20 carries the catheter 12 with it.

In use, a sterile catheter with an inserted sterile trocar is removed from a sterile package, taking care that the catheter does not slip off the trocar. The surgeon grasps the proximal end of the catheter typically with four fingers wrapping around the catheter and thumb resting on the base of the trocar. The device is thrust into a patient's chest whereby the piercing point of the trocar incises the chest. The catheter, carried by the trocar, is forced through the incision into the chest cavity of the patient. After an appropriate length of the catheter has been inserted into the chest cavity, the trocar is removed from the catheter and a drainage conduit or device is coupled to the proximal end of the catheter in order to pull or drain fluids from the chest of the patient.

The prior art trocar catheter, as detailed in FIG. 1, has several disadvantages. First, the piercing point 22 of the trocar is exposed and can cause accidental pricks and punctures while the device is being handled prior to incision. Moreover, after the catheter is installed in the chest cavity and the trocar is removed from the catheter, the piercing point of the trocar is again exposed and presents the same dangers. Second, with the prior art device there is no effective means for preventing the catheter from sliding off the trocar when the device is being handled by the surgeon prior to incision. As both the trocar and the catheter must be sterile, the danger of the catheter detaching from the trocar before installation is that the catheter will fall onto a nonsterile surface and will be unusable.

Other known catheters include suprapubic catheters such as shown in FIG. 1a which is used with the a similar trocar as shown in FIG. 1, except that the trocar has a sharp beveled tip 222. The suprapubic catheter 212 is also a flexible partially elastic catheter having an inner diameter defining a lumen 213. The lumen 213 has a stepped smaller diameter portion 216 at the distal end 214 of the catheter. The proximal end 218 of the catheter is flared for coupling with a drainage conduit or syringe (not A metal trocar like the one shown in FIG. 1 is inserted shown). A metal trocar like the one shown in FIG. 1 is inserted into the lumen 213 of the catheter 212. The suprapubic catheter is also provided with a 5cc latex retention balloon 225 near its distal end 214 and a collar 223 for optional anchoring to the skin with sutures or tape after the catheter is inserted into the suprapubic region. Proximal of the collar 223, Y-ports 219 and 221 are provided for inflation and irrigation through luer connections 219a and 221a.

While the suprapubic catheter has many enhancements for use in the suprapubic region, it still relies on the same kind of trocar as the chest catheter of the prior art and suffers from the same disadvantages.

SUMMARY OF THE INVENTION

It is therefore an object of the invention to provide a trocar catheter where the piercing point of the trocar is guarded to prevent accidental punctures and pricks.

It is also an object of the invention to provide a trocar catheter where the catheter is secured from accidental detachment from the trocar prior to incision.

It is another object of the invention to provide automatic mechanism for guarding the piercing point of the trocar prior to incision where the automatic mechanism automatically exposes the piercing point of the trocar when an incision is being made.

It is a further object of the invention to provide an automatic mechanism for guarding the piercing point of the trocar during incision so as to prevent accidental piercing of organs or walls.

Another object of the invention is to provide an automatic mechanism for guarding the piercing point of the trocar subsequent to incision where the automatic mechanism automatically guards the piercing point of the trocar when the trocar is removed from the catheter In accord with these objects which will be discussed in detail below, the trocar catheter of the present invention includes a catheter substantially the same as the prior art catheters and having a stepped diameter lumen, and a trocar having a spring biased safety shield and means for securing the catheter to the trocar. The distal end of the trocar is provided with a three stepped coaxial bore for mounting a piercing point rod, a coaxial spring, and the spring biased safety shield. The spring biased safety shield has an outer diameter slightly smaller than the stepped smaller diameter of the lumen at the distal end of the catheter so that it can extend therethrough. The piercing point rod has a stepped outer diameter with a larger diameter distal end which tapers to a point and a smaller diameter proximal end. The safety shield has a stepped inner diameter which mates with the stepped outer diameter of the piercing point rod. The larger diametered portion of the stepped inner diameter of the safety shield is at the distal end of the safety shield. Thus, the coaxial spring biases the safety shield towards the distal end of the trocar and movement of the safety shield is limited by the first step of the coaxial bore in the distal end of the trocar and the stepped outer diameter of the piercing point rod. The distal end of the safety shield is provided with a circumferential protrusion which is ramped to an outer diameter slightly larger than the stepped smaller diameter of the lumen at the distal end of the catheter. As the catheter is elastic, the ramped protrusion of the safety shield can be forced through the stepped smaller diameter of the lumen by exerting some force and a similar amount of force is required to remove the trocar from the catheter.

Additional objects and advantages of the invention will become apparent to those skilled in the art upon reference to the detailed description taken in conjunction with the provided figures.

BRIEF DESCRIPTION OF THE DRAWINGS

FIG. 1 is a schematic longitudinal cross section of a prior art trocar catheter for chest drainage;

FIG. 1a is a schematic longitudinal cross section of a prior art suprapubic catheter;

FIG. 2 is a view similar to FIG. 1, but of the trocar catheter of the invention;

DETAILED DESCRIPTION OF THE PREFERRED EMBODIMENTS

Figure 3:
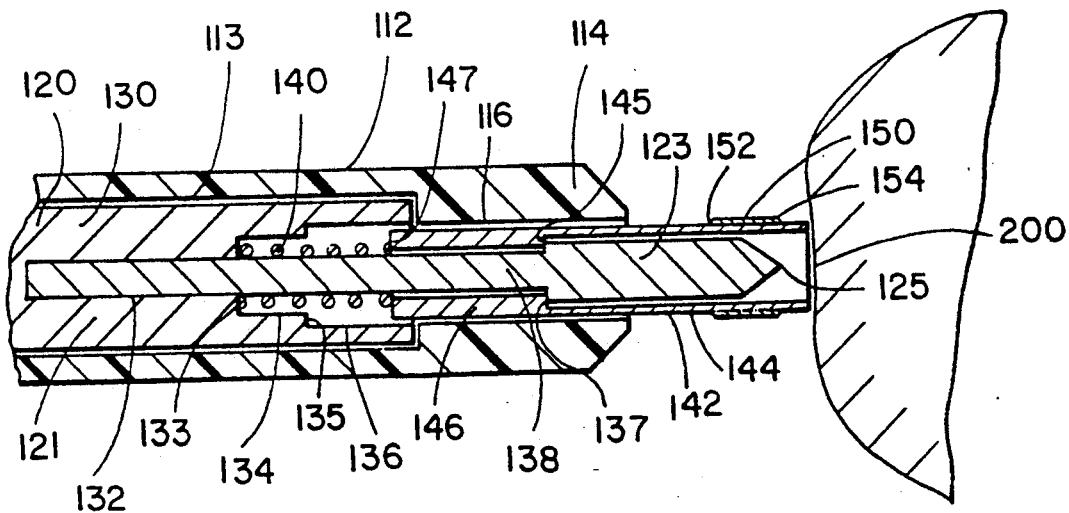
FIG. 3 is a magnified view of the distal end portion of the trocar catheter of FIG. 2, prior to incision.

Referring now to FIGS. 2 and 3, the trocar catheter 110 of the invention comprises a catheter 112 and a trocar 120. The catheter 112 is substantially the same as the prior art catheter 12 seen in FIG. 1 described above and includes a lumen 113 with a distal step 116. The trocar 120 of the invention, however, is quite different from the trocar of the prior art, and includes a rod 121 with a proximal end cap 124 and a hollowed distal end 130, a piercing point rod 122 which is fit into the distal end 130 of rod 121, and a spring loaded shield or safety sleeve 144.

Figure 4:
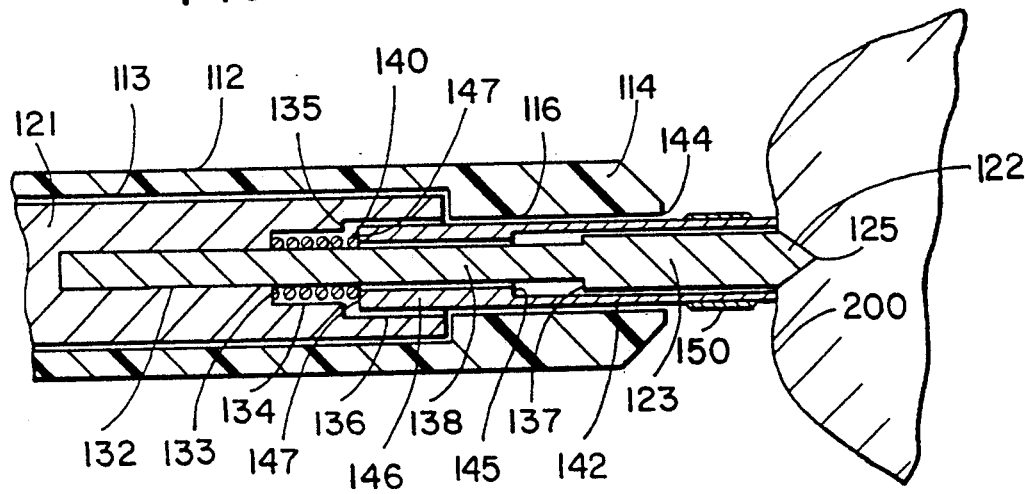
FIG. 4 is a view similar to FIG. 3 but at the point of incision.
Figure 5:
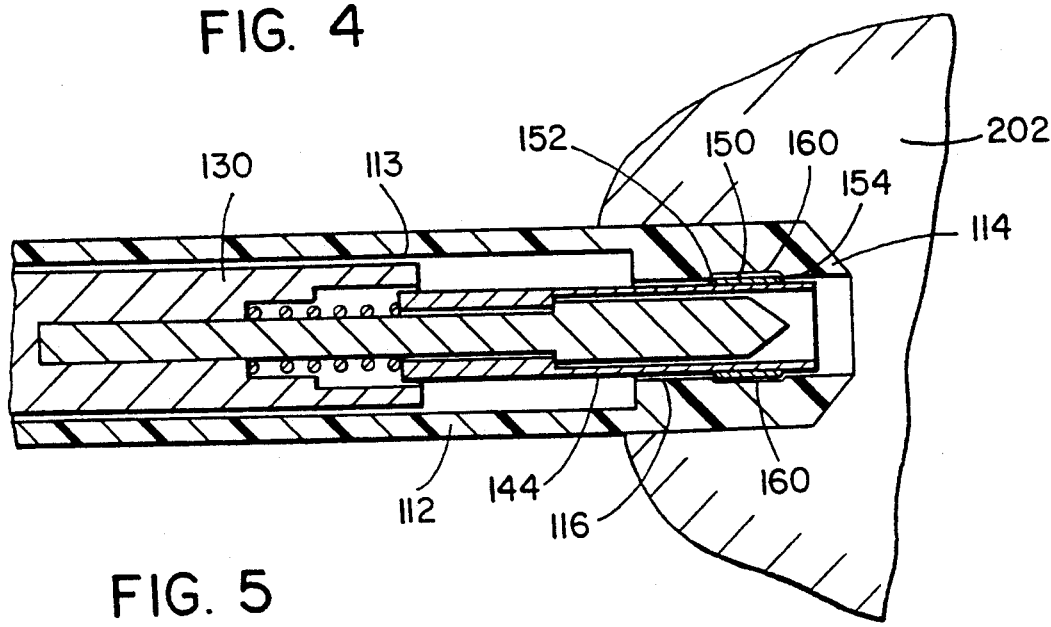
FIG. 5 is a view similar to FIGS. 3 and 4, but after incision and during removal of the trocar from the catheter.

As seen in FIGS. 3-5, the distal end 130 of the trocar rod 121 of the invention is provided with a stepped coaxial bore 132 having a first step 134 and a second larger diameter step 136. Bore 132 extends into the distal end of the trocar rod, and in the preferred embodiment (for a French 13 sized device) has a diameter of approximately 0.055 inches. The first step 134 has an internal diameter of approximately 0.09 inches, while the larger diameter step has an internal diameter of approximately 0.102 inches. The larger diameter step 136 extends a length of approximately 0.185 inches into the distal end of the trocar and the first step 134 extends approximately 0.205 inches further into the distal end of the trocar.

The piercing point rod 122 has a larger outer diameter distal portion 123 which tapers to a point 125. Proximal the distal portion 123 is a stepped smaller outer diameter shaft 138 which is press fit into bore 132. The safety shield 142 in the form of a sliding collar extends around the piercing point rod 122. The collar 142 has an outer diameter slightly smaller than the smaller diameter portion 116 of lumen 113. The inner diameter of the collar 142 includes a larger inner diameter portion 144 and a stepped smaller inner diameter portion 146. The smaller inner diameter portion 146 fits around shaft 138 of the piercing point rod, and the larger inner diameter portion 144 fits around the larger diameter portion 123 of piercing point rod 122. A seat 137 formed between the larger diameter portion 123 and the shaft 138 of the piercing point rod 122 and a stop surface 145 formed between the larger and smaller diameter portions of the safety shield 142 limit the axial movement of the safety shield in the distal direction as shown in FIG. 3. A coaxial spring 140 fits around the shaft 138 behind the safety shield 142. One end of the spring abuts seat 133 formed by the first step 134 in the distal end 130 of rod 121, and the other end of the spring abuts the proximal surface 147 of the safety shield. As will be appreciated from comparing FIGS. 3 and 4, axial movement of the safety shield in the proximal direction is limited by a stop surface 135 formed by the larger diameter step 136, as well as by spring 134.

In assembling the distal end of trocar 120, the safety sleeve 144 is placed over the shaft 138 of the piercing point rod 122 until the larger inner diameter portion 144 of the sleeve 142 surrounds the larger diameter portion 123 of the piercing point rod 122. Spring 140 is then placed over the shaft 138, and the shaft 138 is then press fit into the small diameter bore 132 of the rod 121. It will be appreciated that the assembled trocar 120 is provided with a spring biased axially movable safety shield covering the piercing tip 125 as shown in FIG. 3. It will also be appreciated that the length of the piercing point rod 122 and the length of the safety shield 142 are chosen so that the shield covers the tip 125 when biased by spring 140 as shown in FIG. 3. In a preferred embodiment of the invention, the shield extends approximately 0.1 inches beyond the piercing tip 125 when stop 145 of the shield abuts the seat 137 of the larger diameter portion 123 of the piercing point rod 122. It will therefore be appreciated that when the trocar catheter 110 of the invention is thrust into the chest 200 of a patient, the safety sleeve 142 is pressed back against spring 140, thereby exposing the piercing tip 125 so that an incision can be made as shown in FIG. 4. However, prior to incision, the spring biased safety shield guards the piercing point against accidental punctures or pricks. Likewise, during incision, but after the piercing tip has passed through the chest wall and into the chest cavity, the spring biased safety shield extends distally and guards the piercing point from puncturing a lung or other organ or wall.

As seen in FIGS. 3 and 4, the safety shield 142 is provided with an outer protrusion 150 which rises approximately 0.001 to 0.002 inches from the outer surface of the shield at a point near the distal end of the shield. It will be understood from comparing FIGS. 4 and 5 that the protrusion 150 inhibits movement of the shield through the small diameter portion 116 of the lumen 113 of the catheter 112. Correspondingly, the protrusion 150 inhibits movement of the catheter in a distal direction relative to the trocar. It will thus be appreciated that when the trocar is inserted into the lumen of the catheter such that the safety shield extends beyond the distal end 114 of the catheter as shown in FIGS. 3 and 4, the catheter is inhibited from slipping off the trocar by action of the protrusion 150. Nevertheless, the protrusion 150 must be able to pass through the smaller diameter portion 116 of the lumen 113 in order that the trocar be inserted into the catheter prior to its use and in order that the trocar be removed from the catheter after the catheter is installed. To aid in the passage of the protrusion 150 through the lumen, ramped edges 152, 154 are provided on the protrusion 150. These edges allow the protrusion to wedge its way inside the narrow portion 116 of lumen 113 so that the safety shield can be forced through with a minimum of force, while at the same time preventing inadvertent slippage of the catheter over and off the trocar.

Turning now to FIG. 5, it will be recalled that the catheter 112 is made of an elastic material. It is important that the distal end 114 of the catheter be sufficiently elastic such that the protrusion of the safety shield can stretch the smaller diameter portion 116 of the lumen and pass through it. FIG. 5 shows the catheter 112 inserted into the chest cavity 202 of a patient and the trocar in a partial stage of removal from the catheter. It will be appreciated that as the trocar is withdrawn from the catheter (while the catheter is held in place by the surgeon or an assistant), the protrusion 150 on the shield 144, aided by ramped edge 152, stretches the lumen as shown by lines 160. It will be appreciated that the elasticity and resilience of the catheter at its distal end 114 should be such that the narrow portion 116 of the lumen 113 resumes its small diameter after the protrusion has passed through it.

According to a presently preferred embodiment, the piercing point, spring, and the safety shield are all constructed of stainless steel. The remainder of the trocar is preferably constructed of aluminum. The tip 125 of the piercing point rod is preferably conical with a 60° apex for a chest trocar, while the piercing point rod for a suprapubic trocar is preferably formed as a beveled cylinder as seen in FIG. 1a.

Figure 6:
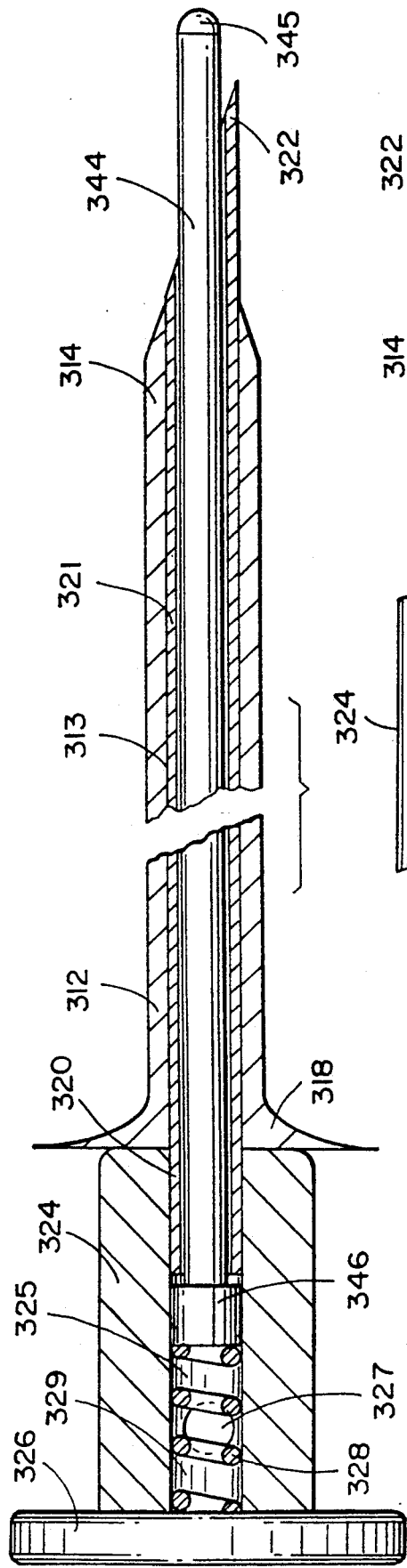
FIG. 6 is a magnified longitudinal cross sectional view of another embodiment of a suprapubic trocar catheter.
Figure 6A:
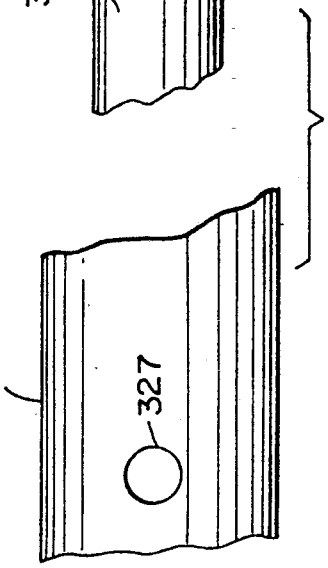
FIG. 6a is a partial top view of the proximal and distal ends of the trocar catheter of FIG. 6 prior to incision.
Figure 6B:
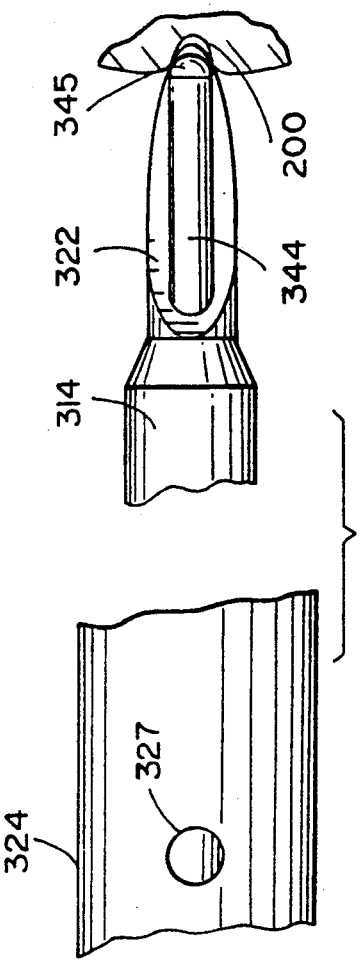
FIG. 6b is a view similar to FIG. 6a but at the point of incision.

FIGS. 6, 6a and 6b show another embodiment of a trocar catheter with spring biased safety means. In this embodiment, a urinary or suprapubic catheter 312 has a relatively constant throughbore 313 (as opposed to the stepped throughbores of the catheters of FIGS. 1-5) extending from its proximal end 318 to its distal end 314. Trocar 321 is formed as a hollow tube member with a piercing point 322 made by a beveled cut in the distal end of the trocar. Proximal end 320 of trocar 321 is mounted in a handle or cap member 324 which is preferably provided with a proximal flange 326 and an axial bore 339. A safety rod 344 is inserted inside trocar 321 and is axially movable with respect thereto. The distal end of the safety rod is provided with a blunt tip 345 and the proximal end is provided with an indicating stop 346 which resides in the axial bore 329 of the handle member 324. A spring 328 biases the indicating stop 346 and thereby the safety rod 344 in the distal direction so that the blunt tip extends sufficiently beyond the piercing point 322 of trocar 321 as shown in FIGS. 6 and 6a. Thus, the trocar 321, safety rod 344, and spring 328 together appear similar to a Veress-type needle, except that the assembly is considerably longer (e.g., about nine inches in length), that the safety rod 344 need not be hollow with a distal port, and that it is used through a suprapubic or urinary catheter. The dimensions of the rod 344, stop 346, bore 339 and spring 328 are such that the blunt tip 345 may be pressed inward against the spring 328 to expose the piercing point 322 of the trocar as seen in FIG. 6b.

In accord with a preferred embodiment, the handle member 324, which is typically opaque, is provided with a viewing window 327 through which the indicating stop 346 may be viewed. By providing the indicating stop with a color such as red, the physician can readily determine the position of the blunt tip 345 relative to the piercing point 322. For example, when the blunt tip is in the safety position prior to incision as shown in FIG. 6a, the indicating stop is biased by spring 328 to a position where it is not visible through window 327. However, at the point of incision, as shown in FIG. 6b, when the blunt tip is pressed back against spring 328, the indicating stop 346 is moved to a position where it is visible through the window 327 thereby indicating that the piercing point 322 of the trocar is exposed.

It will be appreciated that the distal end of the trocar in this embodiment could also be provided with one or more protrusions as described above with reference to the first embodiment so that it could be used with a stepped catheter and so that the catheter can be kept from falling off the trocar during handling prior to incision.

There has been described and illustrated herein trocar catheters with safety mechanisms. One safety mechanism comprises an outer sleeve which further includes means for preventing the catheter from unintentionally detaching from and slipping off the trocar prior to incision and installation of the catheter. Another safety mechanism is similar to an extended Veress-type needle mechanism. While particular embodiments of the invention have been described, it is not intended that the invention be limited thereto, as it is intended that the invention be as broad in scope as the art will allow and that the specification be read likewise. Thus, while particular dimensions and materials have been disclosed, it will be appreciated that other materials and dimensions could be utilized. Also, while the distal end of one embodiment of the trocar has been described as having a three stepped internal bore, it will be appreciated that the essence of the invention could be accomplished with a two stepped bore. Moreover, while the means for preventing the catheter from slipping off the trocar has been shown as a protrusion, it will be appreciated that other types of surface projections could be used as well and that the projections need not complete encircle the safety sleeve. It will also be appreciated that the trocars of the invention can be used with virtually any kind of flexible catheter including the prior art catheters shown in FIGS. 1 and 1a. In some embodiments, however, it is preferred that the catheter has a stepped diameter lumen substantially as shown. It will therefore be appreciated by those skilled in the art that yet other modifications could be made to the provided invention without deviating from its spirit and scope as so claimed.

We claim:

1. A trocar which extends through and for use with a catheter having a stepped diameter lumen, wherein said trocar is inserted into the lumen of the catheter and said trocar is used to incise a patient and install the catheter after which the trocar is removed from the lumen of the catheter, said trocar comprising:

a) a safety sleeve having a distal larger inner diameter portion and a proximal smaller inner diameter portion;

b) a piercing point rod having a distal larger outer diameter portion tapering to a piercing tip and a proximal smaller outer diameter portion, said safety sleeve being movable axially over said piercing point rod, said distal larger inner diameter portion being movable over said distal larger outer diameter portion and said proximal smaller inner diameter portion being movable over said proximal smaller outer diameter portion;

c) a spring carried on said proximal smaller outer diameter portion of said piercing point rod; and d) a trocar rod having a distal end with a stepped receiving bore which receives said proximal smaller outer diameter portion of said piercing point rod, said spring, and said safety sleeve, said receiving bore having a relatively small diameter portion into which said proximal smaller diameter portion of said piercing point rod is mounted, a first seat for biasing said spring against said safety sleeve to a first position whereby said piercing tip is covered by said safety sleeve, and a relatively large diameter portion for receiving a portion of said safety sleeve against said spring.

2. A trocar according to claim 1, wherein:
the stepped diameter lumen has a larger diameter in a proximal portion of the catheter and a smaller diameter in a distal portion of the catheter, and
said safety sleeve has an outer diameter which fits through said distal portion of the lumen.

3. A trocar according to claim 2 wherein the catheter is elastic and, said trocar further comprises:
e) means for inhibiting movement of said safety sleeve through the distal portion of the lumen.

4. A trocar according to claim 3, wherein:
said means for inhibiting movement of said safety sleeve through the distal portion of the lumen comprises a surface protrusion on a distal outer surface of said safety sleeve.

5. A trocar according to claim 4, wherein:
said surface protrusion has a ramped edge.

6. A trocar according to claim 1, wherein:
when said trocar is inserted into said lumen of said catheter, said piercing tip extends beyond a distal end of the catheter and said safety sleeve extends beyond a distal end of said piercing tip.

7. A trocar according to claim 6, wherein:
said safety sleeve is movable against said spring to a second position whereby said distal end of said piercing tip is uncovered by said safety sleeve.

8. A trocar according to claim 1, wherein:
said receiving bore further includes a relatively intermediate diameter portion between said relatively small diameter portion and said relatively large diameter portion and a stop between said relatively intermediate diameter portion and said relatively large diameter portion, said stop limiting proximal movement of said safety sleeve.

9. A trocar according to claim 7, wherein:
said receiving bore further includes a relatively intermediate diameter portion between said relatively small diameter portion and said relatively large diameter portion and a stop between said relatively intermediate diameter portion and said relatively large diameter portion, said stop limiting proximal movement of said safety sleeve.

10. A trocar according to claim 9, wherein:
the stepped diameter lumen has a larger diameter in a proximal portion of the catheter and a smaller diameter in a distal portion of the catheter, and
said safety sleeve has an outer diameter which fits through said distal portion of the lumen.

11. A trocar according to claim 10 wherein the catheter is elastic and, said trocar further comprises:
e) means for inhibiting movement of said safety sleeve through the distal portion of the lumen.

12. A trocar according to claim 11, wherein:
said means for inhibiting movement of said safety sleeve through the distal portion of the lumen comprises a surface protrusion on a distal outer surface of said safety sleeve.

13. A trocar according to claim 12, wherein:
said surface protrusion has a ramped edge.

14. A trocar according to claim 1 in combination with said catheter having a stepped diameter lumen.

15. A trocar according to claim 14, wherein:
said catheter having a stepped diameter lumen is one of a chest catheter and a suprapubic catheter.

16. A trocar according to claim 4 in combination with said catheter having a stepped diameter lumen.

17. A trocar according to claim 16, wherein:
said catheter having a stepped diameter lumen is one of a chest catheter and a suprapubic catheter.

18. A trocar according to claim 9 in combination with said catheter having a stepped diameter lumen.

19. A trocar according to claim 18, wherein:
said catheter having a stepped diameter lumen is one of a chest catheter and a suprapubic catheter.

* * * * *